(12) United States Patent
Negishi

(10) Patent No.: US 8,716,683 B2
(45) Date of Patent: May 6, 2014

(54) ION BEAM PROCESSING SYSTEM AND SAMPLE PROCESSING METHOD

(71) Applicant: JEOL Ltd., Tokyo (JP)

(72) Inventor: Tsutomu Negishi, Tokyo (JP)

(73) Assignee: JEOL Ltd., Tokyo (JP)

( * ) Notice: Subject to any disclaimer, the term of this patent is extended or adjusted under 35 U.S.C. 154(b) by 0 days.

(21) Appl. No.: 13/680,292

(22) Filed: Nov. 19, 2012

(65) Prior Publication Data

US 2013/0134325 A1 May 30, 2013

(30) Foreign Application Priority Data

Nov. 28, 2011 (JP) ................................ 2011-259043

(51) Int. Cl.
*G01N 1/44* (2006.01)
*H01J 49/04* (2006.01)

(52) U.S. Cl.
USPC ................... 250/492.3; 250/441.11; 250/289

(58) Field of Classification Search
USPC ..................... 250/492.3, 289, 441.11; 850/18
See application file for complete search history.

(56) References Cited

U.S. PATENT DOCUMENTS

| 3,580,685 A * | 5/1971 | Eriksson ..................... 356/244 |
| 3,886,358 A * | 5/1975 | McLaughlin et al. ........ 250/289 |
| 7,722,818 B2 * | 5/2010 | Hasegawa et al. ............ 422/502 |
| 2011/0031139 A1 * | 2/2011 | Macor .......................... 206/232 |

FOREIGN PATENT DOCUMENTS

JP 2011192521 A 9/2011

* cited by examiner

*Primary Examiner* — Jack Berman
*Assistant Examiner* — Kevin Chung
(74) *Attorney, Agent, or Firm* — The Webb Law Firm

(57) ABSTRACT

An ion beam processing system (100) processes the sample (S) mounted on a sample stage (30) by irradiating the sample with an ion beam in a sample chamber (2). The system has a sample container (20) including a cover portion (26) formed to be detachably mountable to a base portion (24), the sample stage (30) on which the container (20) is detachably mountable, and cover mounting/dismounting apparatus (40) for mounting and dismounting the cover portion (26) from outside the sample chamber (2).

5 Claims, 7 Drawing Sheets

ION BEAM PROCESSING SYSTEM AND SAMPLE PROCESSING METHOD

BACKGROUND OF THE INVENTION

1. Field of the Invention

The present invention relates to an ion beam processing system and sample processing method.

2. Description of Related Art

Methods for mechanically polishing samples are known as sample preparation methods for observations and analyses using electron microscopy. In a mechanical polishing method, however, a force acts on the worked surface. Therefore, softer parts may be deleted earlier, forming unevenness, or the softer parts may be crushed. Furthermore, a harder material may be buried in softer parts. Consequently, with a method of mechanical polishing, it has been difficult to smoothly polish junctions or boundaries of materials of different hardnesses. In this way, with a mechanical polishing method, it has been difficult to prepare a sample cross section without varying the morphology or composition of the sample.

In view of this problem, JP-A-2011-192521, for example, discloses an ion beam processing system for processing samples by a cross section polisher (CP) that prepares a cross section in a manner relatively unaffected by the processing work. In the ion beam processing system disclosed in JP-A-2011-192521, a shield plate for blocking the ion beam is mounted over the sample to control the irradiated region. The beam is directed at the region of the sample not shielded by the shield plate to process the sample.

In recent years, electric vehicles have attracted attention due to environmental issues, energy problems, and so on. Developments of lithium-ion batteries for such electric vehicles have been accelerated. In the course of development of lithium-ion batteries, the structure is observed and an elemental analysis is made. Because lithium is a material readily reacting with oxygen and nitrogen, it is necessary to perform all processing steps including sample preparation, observation, and analysis under an environment isolated from the atmosphere.

The ion beam processing system disclosed in JP-A-2011-192521 has the problem that the sample is exposed to the atmosphere either when the sample is loaded into the processing system or until the processed sample is transferred and introduced into an instrument such as an electron microscope for observation or analysis of the sample. As a result, the sample such as lithium will change in quality.

SUMMARY OF THE INVENTION

In view of the foregoing problems, the present invention has been made. According to some aspects of the invention, an ion beam processing system and sample processing method can be offered which is capable of preventing a sample from deterioration in quality caused by exposure to the atmosphere.

An ion beam processing system associated with the present invention processes a sample mounted on a sample stage by irradiating the sample with an ion beam in a sample chamber. The system has: an ion source for producing the ion beam; a sample container including a sample support portion on which the sample is placed, a base portion for supporting the sample support portion, and a cover portion formed so as to be detachably mountable to the base portion and forming a sealed space for tightly closing off the sample; the sample stage on which the sample container can be detachably mounted; and cover mounting/dismounting apparatus for mounting and dismounting the cover portion from outside the sample chamber. The sample container is provided with a window to permit the sealed space to be visually checked from outside the sample container.

This ion beam processing system makes it possible to align the sample after being mounted on the sample stage without being exposed to the atmosphere. Furthermore, a processed sample can be inserted in the sample container without being exposed to the atmosphere. Hence, the sample can be prevented from being exposed to the atmosphere during processing of the sample and until the sample is introduced into an instrument for observation or analysis of the sample after the processing. Thus, the sample is suppressed from being deteriorated in quality.

The ion beam processing system associated with the present invention may further comprise a shield plate for shielding a part of the sample from the ion beam. This ion beam processing system makes it possible to restrict the area of the sample irradiated with the ion beam.

The ion beam processing system associated with the present invention may contain a viewer for inspecting the sealed space through the window. With this ion beam processing system, the sample can be aligned without being exposed to the atmosphere.

In the ion beam processing system associated with the present invention, the sample container may have a valve to permit gas to be evacuated from inside the sealed space in response to the pressure difference between the inside and outside of the sealed space. In this ion beam processing system, the pressure inside the sealed space can be made equal to the pressure inside the sample chamber.

A sample processing method associated with the present invention is adapted to process a sample mounted on a sample stage by irradiating the sample with an ion beam in a sample chamber. The method starts with preparing a sample container having a base portion, a cover portion, a sample support portion, a sealed space formed by mounting the cover portion on the base portion, and a window formed to permit the sealed space to be visually checked from outside the sample container. The sample support portion is accommodated in the sealed space along with the sample. Then, the sample container is mounted on the sample stage. The sample is aligned while visually checking its position through the window in the sample container. The cover portion is then removed from the base portion from outside the sample chamber. The sample is processed with the ion beam emitted from an ion source. The cover portion is mounted to the base portion from outside the sample chamber, and the processed sample is tightly closed off.

In this sample processing method, the sample can be mounted on the sample stage and aligned without exposing the example to the atmosphere. Furthermore, the processed sample can be put into the sample container without exposing the sample to the atmosphere. Since the sample is prevented from being exposed to the atmosphere during processing of the sample and until the already processed sample is introduced into an instrument for observation or analysis, the sample can be suppressed from varying in quality.

In the sample processing method associated with the present invention, the sample chamber may be in an inert gas ambient during the step of mounting the cover portion to the base portion. In this sample processing method, the processed sample can be accommodated in the sealed space in the inert gas ambient.

In the sample processing method associated with the present invention, the sample chamber may be in a reduced pressure state during the step of mounting the cover portion to the base portion. In this sample processing method, the processed sample can be accommodated in the sealed space that is in a reduced pressure state.

Other features and advantages of the present invention will become apparent from the following more detailed description, taken in conjunction with the accompanying drawings, which illustrate, by way of example, the principles of the invention.

DESCRIPTION OF THE PREFERRED EMBODIMENTS

The preferred embodiments of the present invention are hereinafter described in detail with reference to the drawings. It is to be understood that the embodiments described in the following do not unduly restrict the contents of the present invention delineated by the appended claims and that not all the configurations described below are constituent elements of the invention.

1. Ion Beam Processing System

Figure 1:
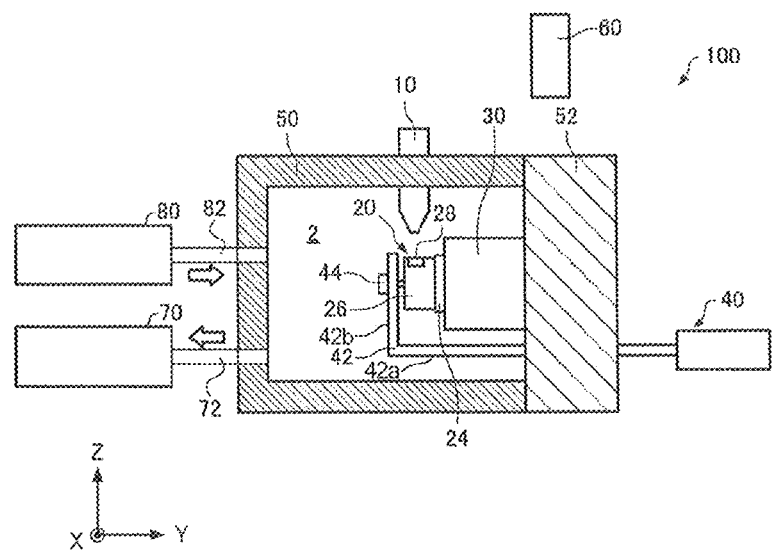
FIG. 1 is a cross section, partially in block diagram, illustrating the structure of an ion beam processing system associated with one embodiment of the present invention.

The structure of an ion beam processing system associated with one embodiment of the present invention is first described. FIG. 1 shows the structure of the ion beam processing system, generally indicated by reference numeral 100. In the state shown in FIG. 1, a sample container 20 is mounted on a sample stage 30.

As shown in FIG. 1, the ion beam processing system 100 is configured including an ion source 10, a lever portion 40 (cover mounting/dismounting apparatus), an enclosure 50, a door portion 52, a viewer 60, exhaust equipment 70, and gas supply equipment 80, as well as the sample container 20 and the sample stage 30.

The ion source 10 is an ion gun that produces a beam of ions such as Ar ions. The ion beam generated by the ion source 10 is directed at a sample. The diameter of the ion beam is about 1 mm, for example.

Figure 2:
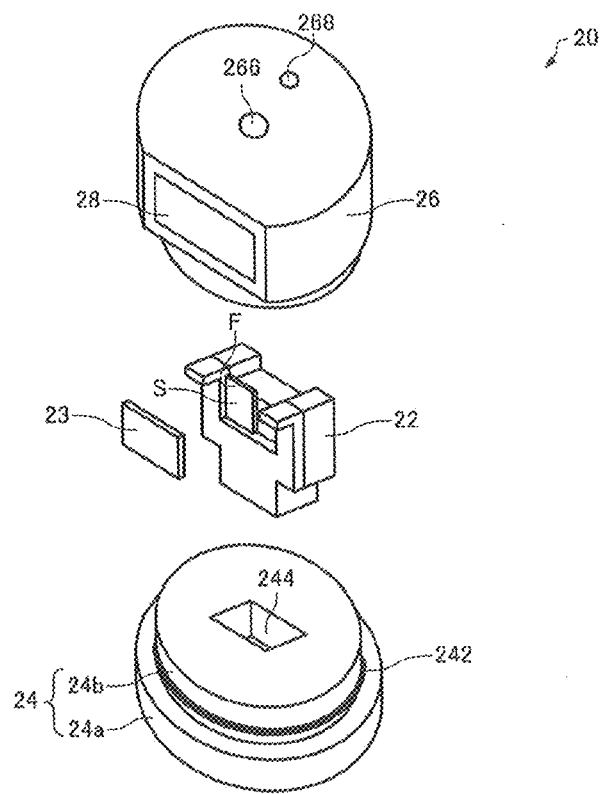
FIG. 2 is a schematic exploded perspective view of a sample container in the ion beam processing system shown in FIG. 1.
Figure 3:
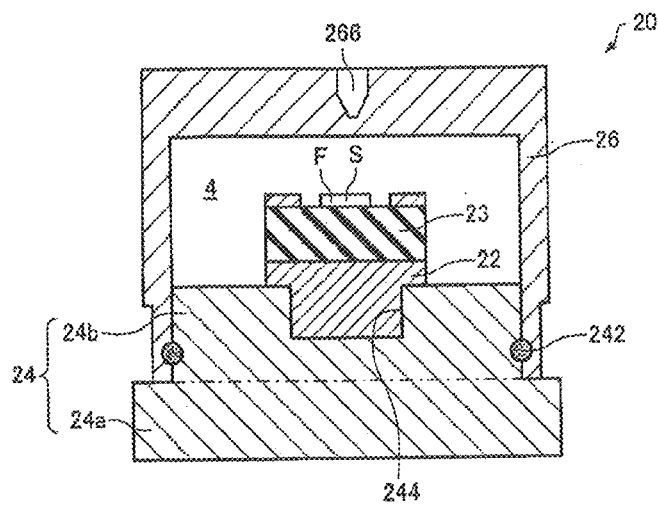
FIG. 3 is a schematic cross section of the sample container shown in FIG. 2.

FIG. 2 is a schematic exploded perspective view of the sample container 20. FIG. 3 is a schematic cross section of the container 20, and shows a state in which the sample S is accommodated in the sample container 20. For the sake of convenience, FIGS. 2 and 3 are taken from a direction different from the viewing direction in FIG. 1.

As shown in FIGS. 2 and 3, the sample container 20 is configured including a sample support portion 22, a base portion 24, and a cover portion 26.

The sample support portion 22 is so formed that the sample S can be placed on it. The sample S may be held to the sample support portion 22. A shield plate 23 is placed on the sample S, which in turn is placed on the sample support portion 22. In the illustrated example, the shield plate 23 is placed on a surface F of the sample S. The shield plate 23 is a member for shielding an unprocessed area of the sample S from the ion beam and so the shield plate 23 can restrict the irradiated area of the sample S. As an example, the shield plate 23 is so positioned that a part of the sample S protrudes from the shield plate 23. Consequently, the portion of the sample S protruding from the shield plate 23 is processed by the beam. As a result, a processed cross section extending along one end surface of the shield plate 23 can be obtained. The shield plate 23 is held to the sample support portion 22, for example, with screws (not shown) or the like. The sample support portion 22 is so formed that it can be detachably mounted, for example, to the base portion 24.

The base portion 24 is so formed that it can support the sample support portion 22. In the illustrated example, the base portion 24 has a first part 24a and a second part 24b both of which are cylindrical in shape. The first part 24a is larger in diameter than the second part 24b and disposed over the second part 24b. The second part 24b has a side surface provided with a groove in which an O-ring 242 is fitted. The second part 24b has a top surface provided with a hole 244 in which the sample support portion 22 is inserted. The sample support portion 22 is inserted in the hole 244 and supported to the base portion 24.

The cover portion 26 is so formed that it can be detachably attached to the base portion 24. When the cover portion 26 is mounted on the base portion 24, a sealed space 4 in which the sample is tightly closed off is formed. In particular, when the cover portion 26 is mounted on the base portion 24, the O-ring 242 provides hermetic sealing between the base portion 24 and the cover portion 26, thus forming the hermetically sealed space 4 that is surrounded by the base portion 24 and cover portion 26.

The cover portion 26 has a top surface provided with a threaded hole 266 into which a screw 44 of the lever portion 40 is inserted. When the screw 44 of the cover portion 26 is inserted in the threaded hole 266, the cover portion 26 is held to the lever portion 40. The cover portion 26 is mounted to or detached from the base portion 24 by manipulating the lever portion 40.

The cover portion 26 has a window 28 that is a member permitting one to visually check the sealed space 4 from outside the sample container 20 as described later. Thus, the sample S can be confirmed while held in the sample container 20. Accordingly, the sample S can be aligned in a manner described later when it is accommodated in the sample container 20. The window 28 is transparent, for example, to visible light, and is a piece of glass. As shown in FIG. 2, the cover portion 26 is mounted to the base portion 24 such that the surface F of the sample S irradiated with the ion beam faces the window 28.

A valve 268 is mounted on the top surface of the cover portion 26 to permit the inside of the sealed space 4 to be evacuated. For example, the valve 268 operates in response to the pressure difference between the inside and outside of the space 4. For instance, the valve 268 has a mechanism for preventing gas from entering the sealed space 4 when the pressure outside the space 4 (outside pressure) is higher than the pressure inside the space 4 (inside pressure). Accordingly, when the outside pressure is higher than the inside pressure, no gas enters the space 4 from the outside. On the other hand, when the outside pressure is lower than the internal pressure, the valve 268 operates to evacuate the gas inside the space 4 to the outside.

The sample support portion 22, base portion 24, and cover portion 26 are made, for example, of stainless steel.

The sample S is mounted on the sample stage 30 along with the sample container 20. The stage 30 is so formed that the sample container 20 can be detachably mounted on the stage 30. The container 20 is mounted on the stage 30 such that the window 28 faces the ion source 10 (in the +Z-direction) as shown in FIG. 1. In the illustrated example, the stage 30 is mounted to the surface of the door portion 52 defining a sample chamber 2. The container 20 is held to the stage 30, for example, with screws (not shown). In this case, the sample container 20 is mounted to the sample stage 30 with screws but no restriction is placed on the structure of the stage 30 as long as the container 20 can be mounted and dismounted.

Figure 4:
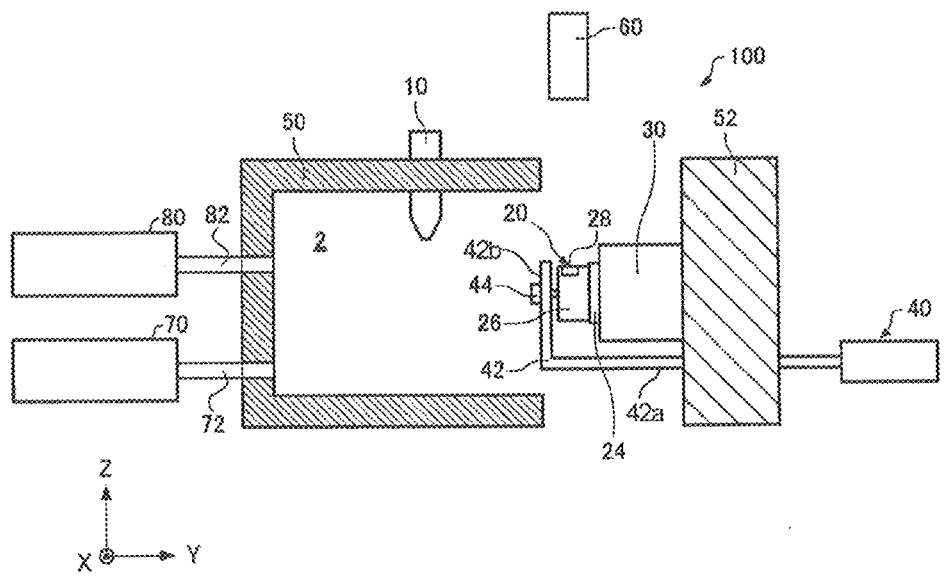
FIG. 4 is a cross section, partially in block diagram, illustrating sample processing steps implemented by the ion beam processing system shown in FIG. 1.

As the door portion 52 is operated, the sample stage 30 moves into or out of the sample chamber 2. Specifically, when the door portion 52 is closed as shown in FIG. 1, the sample stage 30 is received in the sample chamber 2. When the door portion 52 is open as shown in FIG. 4, the stage 30 is disposed outside the sample chamber 2.

The sample stage 30 has a sample moving mechanism (not shown) to move the sample S (sample container 20). The stage 30 moves the sample S by moving the sample container 20, for example, when the door portion 52 is open as shown in FIG. 4. The stage 30 is so formed that the sample S is movable within a plane (X-Y plane) perpendicular to the axis (Z-direction) of the ion beam. Movement of the sample S may be made by driving a motor (not shown) so as to move the sample stage 30. Alternatively, the stage 30 may be moved by manually operating a shaft (not shown) for movement of the stage.

Figure 7:
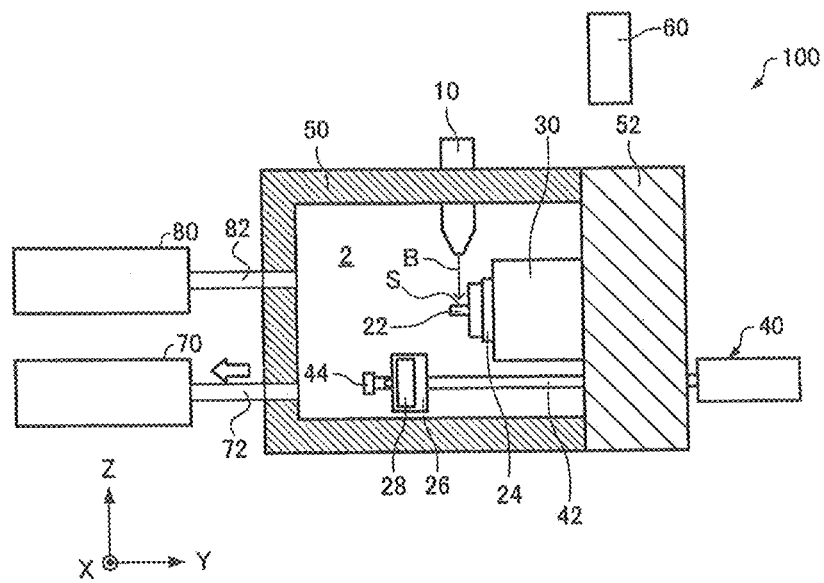
FIG. 7 is a cross section similar to FIG. 4, but showing a still different state.

The lever portion 40 is a member permitting the cover portion 26 to be mounted or dismounted from outside the sample chamber 2. The lever portion 40 has a shaft portion 42 and the screw 44. The shaft portion 42 has a first portion 42a extending along the X-axis and a second portion 42b extending perpendicularly (Z-direction in the example of FIG. 1) to the first portion 42a. That is, the shaft portion 42 assumes an L-shaped form. The first portion 42a extends through the door portion 52. One end of the first portion 42a is located outside the sample chamber 2, while the other end is in the sample chamber 2. A threaded hole is formed near the front end of the second portion 42b, and the screw 44 is inserted in this hole. In the state of FIG. 1, the screw 44 is further inserted in the threaded hole 266 formed in the cover portion 26. Consequently, the cover portion 26 is held to the shaft portion 42. Because of this, the cover portion 26 can be moved by moving the shaft portion 42 from outside the sample chamber 2, and the cover portion 26 can be mounted and dismounted. Furthermore, the cover portion 26 can be moved into a position not hit by the ion beam, for example, by rotating the shaft portion 42 about its axis extending along the X-axis as shown in FIG. 7.

The enclosure 50 and door portion 52 cooperate to form the sample chamber 2. When the door portion 52 of the sample chamber 2 is closed, the chamber 2 is made airtight. An exhaust tube 72 connected to the exhaust equipment 70 is mounted to the enclosure 50. The inside of the sample chamber 2 is depressurized by pumping down the chamber by the exhaust equipment 70 via the exhaust tube 72. Furthermore, a gas supply tube 82 connected to the gas supply equipment 80 is mounted to the enclosure 50. An inert gas such as Ar gas is supplied into the sample chamber 2 from the gas supply equipment 80 via the gas supply tube 82. In consequence, the inside of the sample chamber 2 forms an inert gas ambient. The door portion 52 is opened and closed by moving in the Y-direction. In particular, in FIG. 1, the door portion 52 is in a closed state. If the door portion moves in the +Y-direction from this condition, the door portion is opened as shown in FIG. 4. If the door portion 52 moves in the −Y-direction from the open state shown in FIG. 4, the door portion is closed.

For example, the viewer 60 is a CCD camera. The viewer 60 is so positioned that when the door portion 52 is open as shown in FIG. 4, the viewer can image the sample S in the sealed space 4 through the window 28. The distance between the position of the viewer 60 and the ion source 10, taken in the Y-direction, is the same as the distance between the positions of the sample S assumed when the door portion 52 is open and closed, respectively. Therefore, by aligning the position of the sample S using the viewer 60 while the door portion 52 is open, the sample S can be brought just below the ion source 10, i.e., onto the optical axis of the ion source, when the door portion 52 is closed.

2. Sample Processing Method

A sample processing method according to one embodiment of the present invention is next described. FIGS. 4-10 illustrate steps of processing a sample by this sample processing method. FIGS. 4, 6, 7, 9, and 10 correspond to FIG. 1. In the following description, an example is given in which a sample is processed using the ion beam processing system 100.

First, the sample container 20 holding the sample S therein is mounted on the sample stage 30 as shown in FIG. 4.

The sample S is contained in the sample container 20. One example of method of receiving the sample S in the sample container 20 is described by referring to FIG. 2. As an example, the sample S is placed on the sample support portion 22. The shield plate 23 is put on the surface F of the sample S such that a part (processed portion) of the sample S protrudes from the shield plate 23. The shield plate 23 is held to the sample support portion 22, for example, with screws (not shown). Then, the sample support portion 22 is inserted into the hole 244 in the base portion 24. As a result, the sample support portion 22 is supported by the base portion 24. Subsequently, the cover portion 26 is mounted on the base portion 24. Consequently, hermetic sealing is provided between the cover portion 26 and the base portion 24 by the O-ring 242, and the sealed space 4 is formed. The sample S is received in this space 4. The cover portion 26 is mounted on the base portion 24 in such a way that the region of the surface F of the sample S protruding from the shield plate 23 can be confirmed through the window 28. The sample S can be accommodated in the sample container 20 because of the steps described so far.

The step of receiving the aforementioned sample S into the sample container 20 is performed, for example, in an ambient of an inert gas (e.g., Ar gas). In particular, this receiving step is carried out, for example, in a glove box in the inert gas ambient. Hence, the sample S can be received in the sample container 20 without exposing the sample S to the atmosphere. Furthermore, the sealed space 4 in the sample container 20 holding the sample S therein can be made an inert gas ambient.

The sample container 20 holding the sample S therein is mounted on the sample stage 30 as shown in FIG. 4. In particular, the container 20 is mounted on the stage 30, for example, with screws (not shown) while the door portion 52 of the ion beam processing system 100 is open. This is done, for example, outside the sample chamber 2. The container 20 is mounted such that the window 28 faces the viewer 60 (+Z-direction in the illustrated example).

Then, the sample S is aligned under the state in which the door portion 52 is open while checking the position of the sample S through the window 28 in the sample container 20. The alignment of the sample S is performed such that the processed portion of the sample S protruding from the shield plate 23 is placed in position. Under this condition, if the door portion 52 is closed and the sample S has moved, the processed portion of the sample S is brought just under the ion source 10 (i.e., on the optical axis of the beam). That is, the position of the processed portion of the sample is so set that the distance between this position and the ion source 10, taken in the Y-direction, is the same as the distance between the positions of the sample S assumed when the door portion 52 is open and closed, respectively, taken in the Y-direction.

Figure 5:
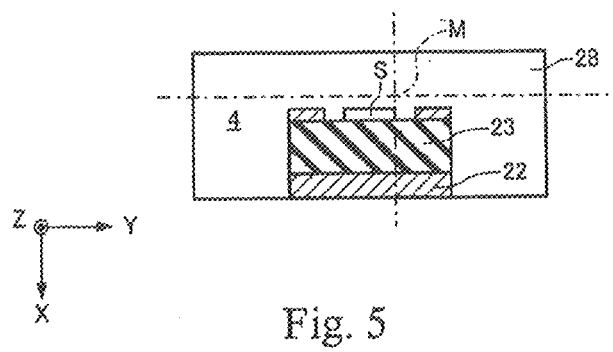
FIG. 5 is a cross section illustrating one sample processing step associated with one embodiment of the invention.

FIG. 5 is a schematic cross section of the sample S taken through the window 28. The viewer 60 superimposes a marker M on the taken image to give indicia indicative of the position of the processed portion, thus providing a reference in aligning the sample S. For this purpose, the sample stage 30 is manipulated to move the sample S, for example, in such a way that the marker M is superimposed on the processed portion of the sample S in the taken image.

Then, the cover portion 26 is held to the lever portion 40 as shown in FIG. 4. In particular, the screw 44 is inserted into the threaded hole 266 (FIG. 2), thus holding the cover portion 26 to the lever portion 40.

Figure 6:
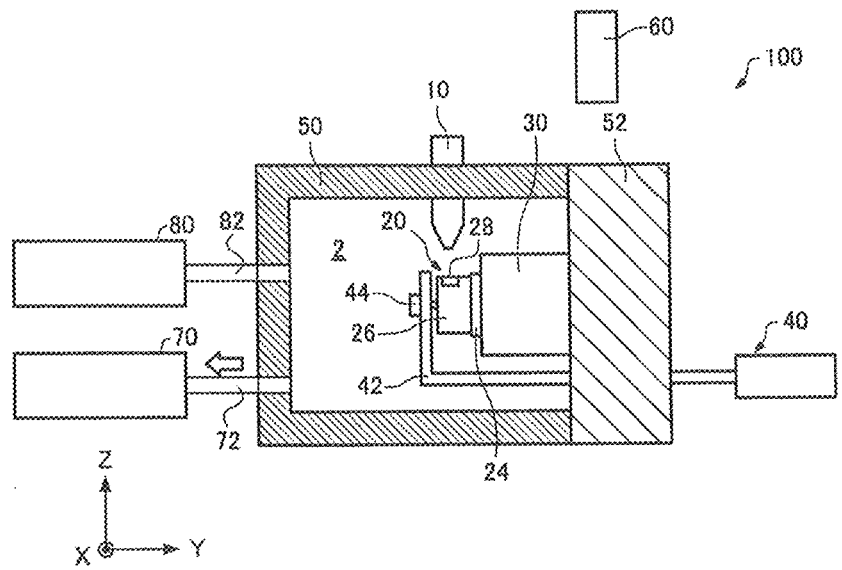
FIG. 6 is a cross section similar to FIG. 4, but showing a different state.

Then, as shown in FIG. 6, the cover portion 26 is closed to close the sample chamber 2 tightly. Since the sample S has been aligned as described previously, the processed portion of the sample S is brought just under the ion source 10 by closing the door portion 52.

Then, the inside of the sample chamber 2 is pumped down by evacuating gas inside the sample chamber 2 by means of the exhaust equipment 70 via the exhaust tube 72. At this time, the pressure (outside pressure) inside the sample chamber 2 becomes lower than the pressure (inside pressure) inside the sealed space 4 of the sample container 20 and so the valve 268 mounted in the cover portion 26 operates to evacuate the inert gas in the sealed space 4. Consequently, the decreased pressure in the sealed space 4 becomes equal to the pressure inside the sample chamber 2.

Then, the cover portion 26 is removed from the base portion 24 from outside the sample chamber 2 by the use of the lever portion 40 as shown in FIG. 7. Specifically, the shaft portion 42 of the lever portion 40 is moved in the −Y-direction to disengage the cover portion 26 from the base portion 24. The cover portion 26 may be placed in a position where the ion beam B does not hit the cover portion, for example, by manipulating the lever portion 40. When the cover portion 26 has been removed from the base portion 24, the sample S and shield plate 23 put on the sample support portion 22 are exposed.

Then, the ion beam B is emitted from the ion source 10 to process the sample S.

Figure 8A:
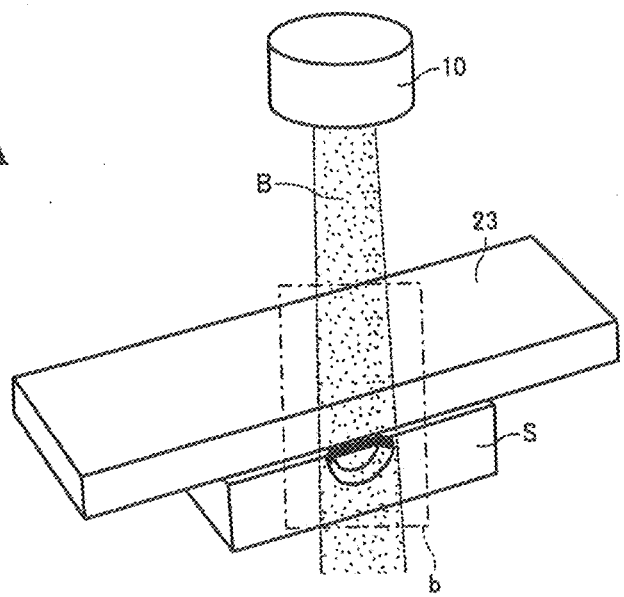
FIG. 8A is a perspective view illustrating one sample processing step associated with one embodiment of the invention.
Figure 8B:
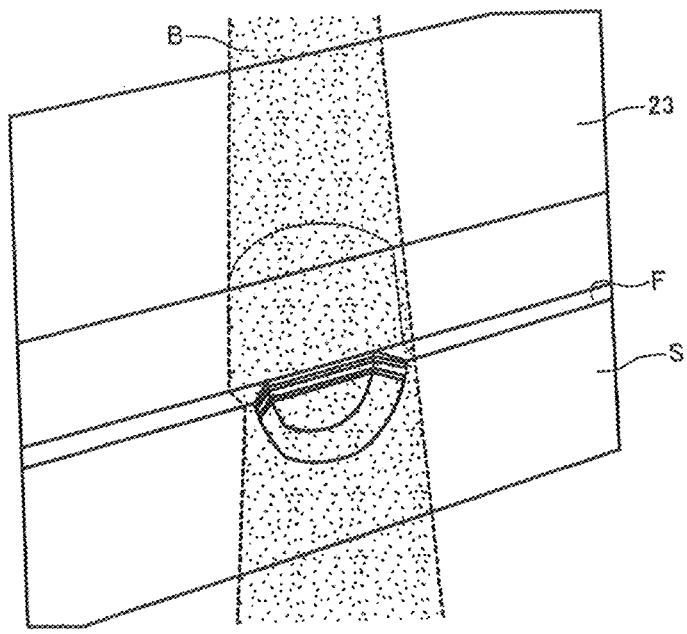
FIG. 8B is an enlarged view of a part of FIG. 8A.

FIG. 8A is a schematic perspective view of the ion source 10, sample S, and shield plate 23. FIG. 8B is an enlarged view of a region B surrounded by the dot and dash line in FIG. 8A. For the sake of convenience, the members other than the ion source 10, sample S, and shield plate 23 are omitted from being shown in FIGS. 8A and 8B. In FIGS. 8A and 8B, the ion beam B hits the processed portion of the sample S which is not shielded by the shield plate 23. Therefore, the portion of the sample S protruding from the shield plate 23 is deleted. As a result, the sample S is processed. A cross section of the sample S can be obtained.

Figure 9:
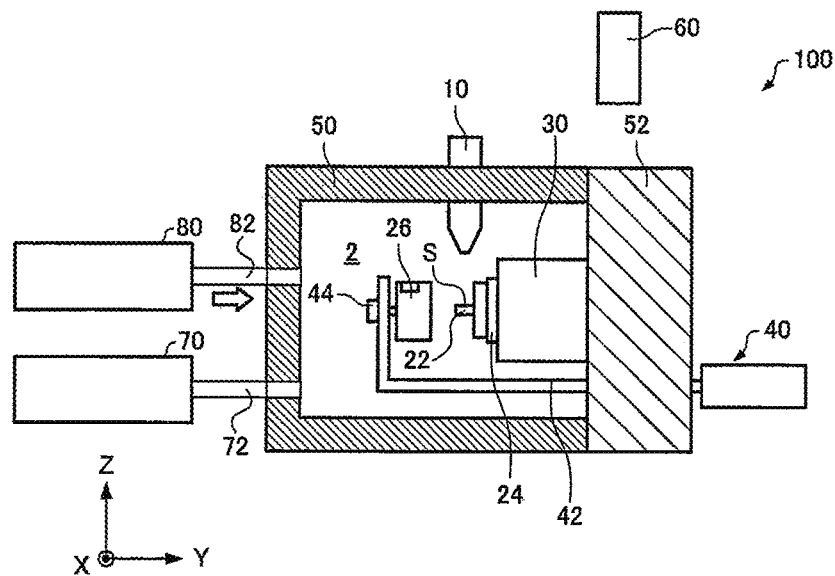
FIGS. 9 and 10 are cross sections similar to FIG. 4, but showing yet different states.
Figure 10:
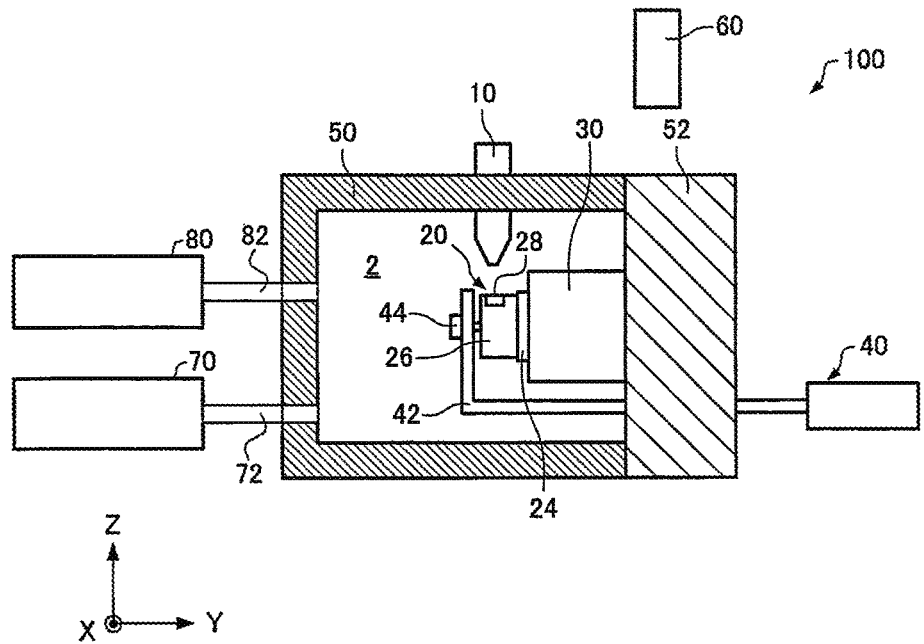

Then, an inert gas such as Ar gas is supplied into the sample chamber 2 as shown in FIG. 9. The inside of the sample chamber 2 becomes an inert gas ambient. The inside of the chamber 2 can be brought to the atmospheric pressure (1 atm). The inert gas is supplied into the chamber 2 by the gas supply equipment 80 via the gas supply tube 82.

Then, the lever portion 40 is manipulated to mount the cover portion 26 onto the base portion 24 from outside the sample chamber 2. As a result, the processed sample S is received in the sealed space 4 in the inert gas ambient.

The door portion 52 is then opened and the sample container 20 is removed from the sample stage 30. Since the processed sample S is accommodated in the sealed space 4 of the container 20, even the outer surface of the sample chamber 2 is not exposed to the atmosphere.

The sample S can be processed because of the steps described so far.

The ion beam processing system 100 associated with the present embodiment can process the sample S using the ion beam B. Consequently, a cross section less affected by the processing work can be obtained than where mechanical polishing is used.

Figure 11:
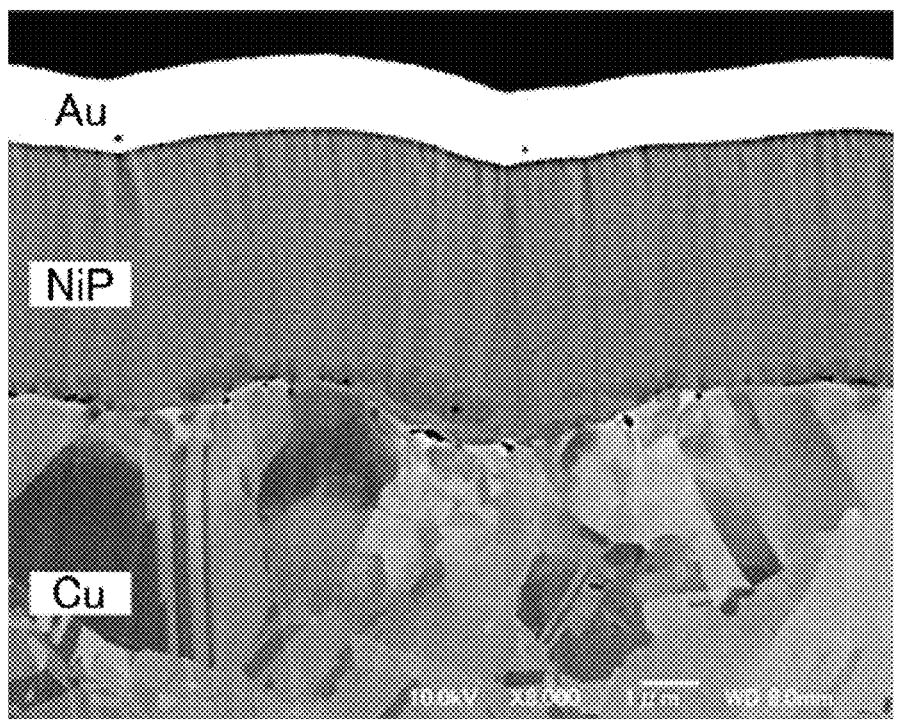
FIG. 11 is an electron microscope photograph of a sample having a cross section that has been processed by an ion beam.
Figure 12:
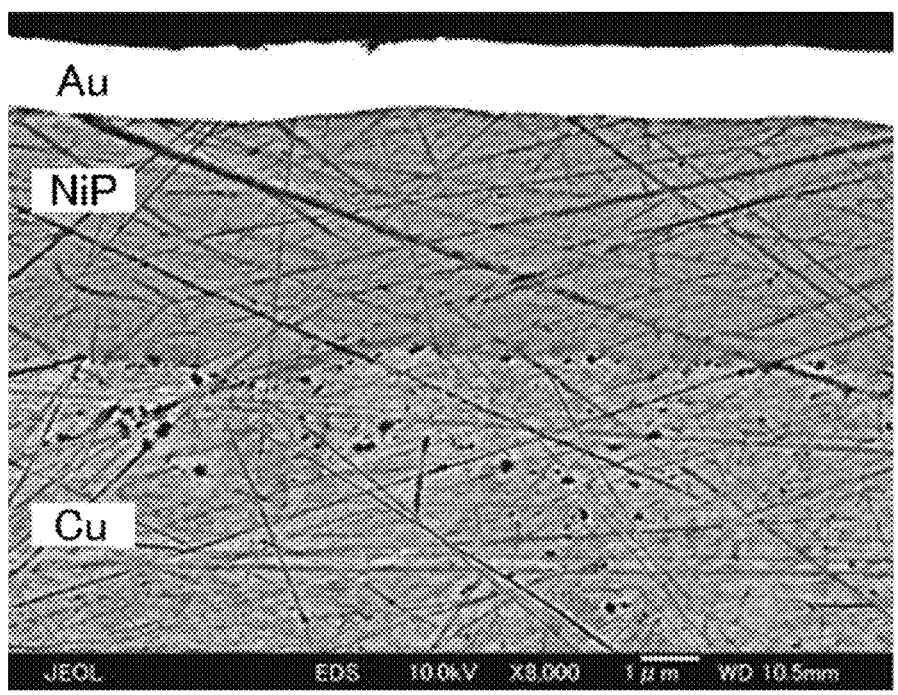
FIG. 12 is an electron microscope photograph of a sample having a cross section processed by mechanical polishing.

FIG. 11 is an electron microscope photograph of a sample having a cross section processed by an ion beam. FIG. 12 is an electron microscope photograph of a sample having a cross section processed by mechanical polishing. Each sample has a structure of layers of Au, NiP, and Cu. As can be seen from FIGS. 11 and 12, a sample cross section which is smoother and less damaged can be obtained by ion beam processing than where mechanical polishing is used. In the electron microscope photograph of FIG. 11, channeling contrast of Cu is obtained. This means that a quite shallow layer (depths of less than 50 nm) in the sample cross section is not destroyed. A cross section less affected by the processing work can be obtained by processing the cross section using an ion beam in this way.

In the present embodiment, the cover portion 26 of the sample container 20 has the window 28 formed such that the sealed space 4 can be visually checked from outside the sample container 20. Therefore, the position of the sample S accommodated in the container 20 can be confirmed through the window 28. Thus, in the ion beam processing system 100, the sample S can be aligned relative to the ion source 10 after mounting the sample S to the sample stage 30 without exposing the sample S to the atmosphere. This can suppress the sample S from varying in quality (i.e., chemical properties, nature, or composition) because the sample is not exposed to the atmosphere during the alignment of the sample S mounted on the stage 30.

The window 28 in the cover portion 26 of the sample container 20 makes it possible to align the sample S outside the sample chamber 2 (i.e., while the door portion 52 is open). This makes it unnecessary that an instrument (such as an electron microscope) for checking the position of the sample be mounted inside the sample chamber 2. Consequently, the system can be simplified.

According to the present embodiment, the ion beam processing system 100 has the lever portion 40 (cover mounting/dismounting apparatus) for mounting and dismounting the cover portion 26 from outside the sample chamber 2 and so the step of removing the cover portion 26 from the base portion 24 and the step of mounting the cover portion 26 to the base portion 24 and tightly closing the cover portion 26 after processing of the sample S can be performed from outside the sample chamber 2.

According to the present embodiment, the sample container 20 can tightly close off the sample S with an inert gas ambient. Accordingly, the sample S is prevented from being exposed to the atmosphere until the processed sample S is introduced into an instrument for observation or analysis; otherwise, the sample S would vary in quality. That is, the sample container 20 can have the function of a transfer vessel.

Processing steps performed until the sample S processed by the ion beam processing system 100 is taken out of the sample container 20, observed, and analyzed are described below.

Figure 13:
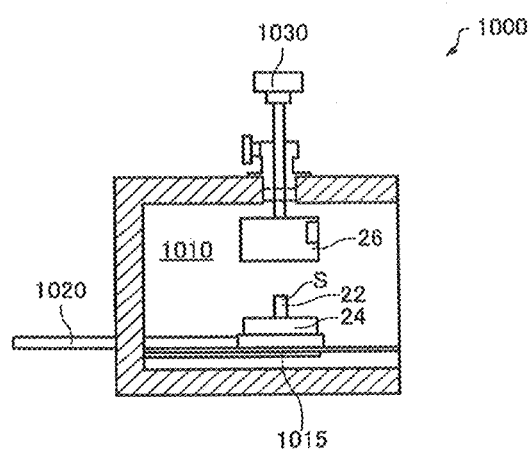
FIG. 13 is a schematic cross section of a sample exchange chamber in a scanning electron microscope.

FIG. 13 is a schematic cross section of a sample exchange chamber (preliminary exhaust chamber) 1010 of a scanning electron microscope (SEM) 1000. The sample container 20 holding the processed sample S therein is formed such that the container can be mounted on a sample stage 1015 of the sample exchange chamber 1010. The base portion 24 of the container 20 is detachably attached to the sample stage 1015. Then, the sample exchange chamber 1010 is depressurized. At this time, the valve 268 (see FIG. 2) of the sample container 20 operates and the inside of the sealed space 4 is evacuated. Therefore, the sealed space 4 and sample exchange chamber 1010 are made equal in internal pressure. Then, the screw at the front end of a cover portion-mounting knob 1030 is inserted into the threaded hole 266 of the cover portion 26. The cover portion 26 is removed from the base portion 24 by manipulating the knob 1030. Thereafter, the base portion 24 carrying the sample S thereon is introduced into the analysis chamber (not shown) of a scanning electron microscope (not shown) by moving the sample stage 1015 by means of a sample exchange rod 1020. As a consequence, the processed sample S can be observed or analyzed without exposure to the atmosphere. In the example provided so far, a scanning electron microscope is used. Other instruments used for observation and analysis of processed samples include X-ray microanalyzer (EPMA) and X-ray photoelectron spectrometer (XPS, ESCA).

According to the present embodiment, it is possible to prevent the sample S from being exposed to the atmosphere during the period beginning with the sample processing step (the processed sample S is received in the sample container 20 after the container 20 is mounted on the sample stage 30) and ending with the introduction of the processed sample S into an instrument for observation or analysis (in the above example, until the sample is introduced into the sample exchange chamber 1010) as described previously. Accordingly, the sample can be prevented from being exposed to the atmosphere during the sample processing step and until the processed sample is introduced into the instrument for observation or analysis; otherwise, the sample would vary in quality. The present embodiment is especially effective for samples of lithium-ion cells, catalysts, and active metals which would vary greatly in quality if exposed to the atmosphere.

It is to be understood that the present invention is not restricted to the above embodiments and that various changes and modifications can be made thereto without departing from the gist and scope of the present invention.

For example, in the above embodiments, the sample chamber 2 is in an inert gas ambient during the step (FIG. 10) of mounting the cover portion 26 to the base portion 24. Therefore, the processed sample S is placed in the inert gas ambient inside the sample container 20. Alternatively, during this step of mounting the cover portion 26 to the base portion 24, the sample chamber 2 may be in a reduced pressure state. In particular, the step of mounting the cover portion 26 to the base portion 24 is performed prior to the step of supplying the inert gas into the sample chamber 2. As a result, the processed sample S is accommodated in the sample container 20 that is in a reduced pressure state.

Furthermore, in the above embodiments, the window 28 is formed in the cover portion 26 as shown in FIGS. 1 and 2. The window 28 may also be formed in the base portion 24 in an unillustrated manner. This can yield the same advantageous effects as the above embodiments.

Having thus described my invention with the detail and particularity required by the Patent Laws, what is desired protected by Letters Patent is set forth in the following claims.

The invention claimed is:

1. An ion beam processing system for processing a sample mounted on a sample stage by irradiating the sample with an ion beam in a sample chamber, said ion beam processing system comprising:
   a sealable enclosure defining the sample chamber;
   an ion source associated with said enclosure for producing the ion beam;
   a sample container including a sample support portion on which the sample is placed, a base portion for supporting the sample support portion, and a cover portion formed so as to be detachably mountable to the base portion and forming a sealed space for hermetically closing off the sample;
   said sample stage supported from the enclosure within the sample chamber on which the sample container can be detachably mounted;
   a cover mounting/dismounting means for mounting and dismounting the cover portion from outside the sample chamber;
   such that after processing the sample can be protected for removal from the enclosure by remounting the cover portion,
   wherein said sample container has a valve permitting gas to be evacuated from inside the sealed space in response to a difference in pressure between the inside and outside of the sealed space, and
   wherein said sample container is provided with a window to permit the sealed space to be visually checked from outside the sample container.

2. An ion beam processing system as set forth in claim 1, further comprising a shield plate for shielding a part of the sample from the ion beam.

3. An ion beam processing system as set forth in any one of claims 1 and 2, further comprising a viewer for inspecting the sealed space through the window.

4. A sample processing method for processing a sample mounted on a sample stage by irradiating the sample with an ion beam in a sealable enclosure defining a sample chamber, said method comprising the steps of:
   mounting a sample container on the sample stage supported from the enclosure, the sample container having a base portion, a cover portion, a sample support portion, and a hermetically sealed space formed by mounting the cover portion on the base portion, the sample support portion being accommodated in the sealed space along with the sample placed on the sample support portion;

aligning the sample while visually checking its position from outside the sample container through a window formed in the sample container to permit a visual check of the sealed space;

removing the cover portion from the base portion from outside the sample chamber;

processing the sample with the ion beam emitted from an ion source; and mounting the cover portion to the base portion from outside the sample chamber and tightly closing off the processed sample, wherein said sample chamber is in an inert gas ambient during the step of mounting the cover portion to the base portion;

whereby the sample is protected for removal from the enclosure.

5. A sample processing method for processing a sample mounted on a sample stage by irradiating the sample with an ion beam in a sealable enclosure defining a sample chamber, said method comprising the steps of:

mounting a sample container on the sample stage supported from the enclosure, the sample container having a base portion, a cover portion, a sample support portion, and a hermetically sealed space formed by mounting the cover portion on the base portion, the sample support portion being accommodated in the sealed space along with the sample placed on the sample support portion;

aligning the sample while visually checking its position from outside the sample container through a window formed in the sample container to permit a visual check of the sealed space;

removing the cover portion from the base portion from outside the sample chamber;

processing the sample with the ion beam emitted from an ion source; and mounting the cover portion to the base portion from outside the sample chamber and tightly closing off the processed sample, wherein said sample chamber is in a reduced pressure state during the step of mounting the cover portion to the base portion; and whereby the sample is protected for removal from the enclosure.

\* \* \* \* \*